(12) United States Patent
Chen et al.

(10) Patent No.: US 7,453,984 B2
(45) Date of Patent: Nov. 18, 2008

(54) REAL-TIME TARGET CONFIRMATION FOR RADIATION THERAPY

(75) Inventors: Shoupu Chen, Rochester, NY (US); Jay S. Schildkraut, Rochester, NY (US); Lawrence A. Ray, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 0 days.

(21) Appl. No.: 11/334,880

(22) Filed: Jan. 19, 2006

(65) Prior Publication Data

US 2007/0165779 A1 Jul. 19, 2007

(51) Int. Cl.
*A61N 5/10* (2006.01)
*H05G 1/70* (2006.01)

(52) U.S. Cl. .............................. 378/65; 378/92; 600/418

(58) Field of Classification Search .................... 378/65, 378/4–20, 92, 165, 204, 210, 201; 600/407, 600/416–418, 425–429
See application file for complete search history.

(56) References Cited

U.S. PATENT DOCUMENTS

| | | | | |
|---|---|---|---|---|
| 5,414,459 | A * | 5/1995 | Bullwinkel | ................... 348/53 |
| 6,201,988 | B1 * | 3/2001 | Bourland et al. | ............. 600/427 |
| 6,307,914 | B1 * | 10/2001 | Kunieda et al. | ............... 378/65 |
| 6,694,169 | B2 * | 2/2004 | Kennedy et al. | ............. 600/426 |
| 6,734,834 | B1 * | 5/2004 | Baram | ........................... 345/8 |
| 6,804,548 | B2 * | 10/2004 | Takahashi et al. | ........... 600/427 |
| 6,961,405 | B2 * | 11/2005 | Scherch | ........................ 378/65 |
| 2003/0048868 | A1 * | 3/2003 | Bailey et al. | .................. 378/65 |
| 2003/0112922 | A1 * | 6/2003 | Burdette et al. | ............... 378/65 |
| 2003/0128034 | A1 * | 7/2003 | Haumann | ................... 324/318 |
| 2005/0049478 | A1 | 3/2005 | Kuduvalli et al. | |
| 2005/0180544 | A1 | 8/2005 | Sauer et al. | |
| 2005/0272991 | A1 * | 12/2005 | Xu et al. | ..................... 600/407 |
| 2006/0079763 | A1 * | 4/2006 | Jeung et al. | ................. 600/428 |
| 2006/0237652 | A1 * | 10/2006 | Kimchy et al. | ......... 250/363.02 |

FOREIGN PATENT DOCUMENTS

| | | |
|---|---|---|
| DE | 100 51 371 A1 | 5/2002 |
| WO | WO 00/61024 | 10/2000 |

OTHER PUBLICATIONS http://www.bmva.ac.uk/bmvc/1997/papers/062/node2.html.
http://www.microopticalcorp.com/Products/HomePage.html.
D. Manke et al., "Novel Prospective Respiratory Motion Correction Approach for Free-Breathing Coronary MR Angiography Using a Patient-Adapted Affine Motion Model" Magnetic Resonance in Medicine, 2003; 50: 122-131.

* cited by examiner

*Primary Examiner*—Edward J Glick
*Assistant Examiner*—Anastasia Midkiff

(57) ABSTRACT

A method for radiation therapy with target recognition has a first target identification system for obtaining first target characteristics within a patient's body. A second target identification system obtains second target characteristics within the body aided by the first target characteristics. A computation means for calculation of three-dimensional coordinates of the target region with respect to a three-dimensional radiotherapy system uses the second target characteristics. Irradiation means for radiotherapy mode adaptation is used in response to the second target characteristics and the calculation of three-dimensional coordinates of the target region.

24 Claims, 12 Drawing Sheets

REAL-TIME TARGET CONFIRMATION FOR RADIATION THERAPY

CROSS REFERENCE TO RELATED APPLICATIONS

Reference is made to commonly-assigned copending U.S. applications Ser. No. 11/039,422, filed Jan. 20, 2005, entitled RADIATION THERAPY METHOD WITH TARGET DETECTION; and Ser. No. 11/221,133, filed Sep. 7, 2005, entitled ADAPTIVE RADIATION THERAPY METHOD WITH TARGET DETECTION by Schildkraut et al., the disclosure of which are incorporated herein.

FIELD OF THE INVENTION

The invention relates generally to radiation therapy systems, and in particular, to real-time target confirmation for radiation therapy.

BACKGROUND OF THE INVENTION

Organ motion and setup error are major causes of target position uncertainty in external radiotherapy for extracranial targets. Uncertainty of target position and shape can result in decreased radiation dose to the target and an increased dose to the surrounding normal tissues. To compensate for the uncertainty of the target position and shape in irradiation process the planning target volume (PTV) must have a larger margin compared to static targets with the same clinical target volume (CTV). This approach increases the probability that the target will receive a lethal dose of radiation. Unfortunately, it also increases collateral damage to surrounding healthy tissues. Some approaches resort to using a learned target motion trajectory model from a 4D CT in the planning phase to guide the radiation beam in the treatment phase, which obviously has the drawback of mismatch between the model trajectory and the actual target motion trajectory.

U.S. Pat. No. 6,804,548 (Takahashi et al.) is directed at a system and method for monitoring irradiation target movement and recognizing irradiation target position in an irradiation process without implanted fiducial markers. The method disclosed in '548 employs a high resolution 3D imaging device such as CT or MRI for taking two sets of 3D images of the irradiation target region (one set, denoted by $H_0$, in radiation planning phase, and another set, denoted by $H_1$, in the treatment phase immediately before the start of irradiation). The method disclosed in '548 uses mutual information measure to compare the irradiation target region extracted from $H_0$ and irradiation target region extracted from $H_1$. As a result of the comparison, the method computes the matching between $H_0$ and $H_1$, and obtains a transformation function incorporating the changes in the irradiation conditions from the irradiation plan. The method disclosed in '548 also employs a real-time imaging device such as an echograph for taking images of the irradiation target region immediately before the start of irradiation and also during the irradiation procedure. Note that for small targets echograph may not be an ideal imaging modality. The real-time image taken immediately before the start of irradiation is denoted by $R_0$. The real-time images taken during the irradiation procedure are denoted by $R_n$. The high resolution image set $H_1$ and real-time image $R_0$ are taken at nearly the same time but with different modalities. The high resolution image set $H_1$ is then superimposed with the real-time image $R_0$ so that the new irradiation plan is reflected in the real-time image $R_0$. During the irradiation treatment, the method '548 compares the real-time images $R_n$ and $R_0$. According to the result obtained by the comparison, the method identifies the portion in the real-time image $R_n$, which corresponds to the irradiation target in the real-time image $R_0$, extracts the target region in the real-time image $R_n$ and computes the position and direction in the 3D coordinate system in the work space for measurement. The method makes a decision as to whether the target tumor is present or not in the region expected in the irradiation plan. To compute the exact position of the target, the method disclosed in '548 installs 3D position and direction sensors such as infrared rays, ultrasound, or magnet on the treatment table, real-time imaging device and high resolution imaging device to find relative position and direction between them.

Marker-less target position monitoring during radiation treatment is a needed feature for radiotherapy to increase accuracy and mitigate damages to normal tissues. However, it is known that extracranial targets may change their shape due to tissue deformation during a bodily process, e.g. a respiration cycle. Furthermore, targets may shrink after a number of fractions of treatment. Therefore, shape tracking is also very much desirable especially for conformal radiation by using automatic beam shaping device such as a multi-leaf collimator (MLC).

Methods of using position and direction sensors to find relative position and orientation of imaging devices to a reference 3D system only solves the problem of extrinsic parameters (e.g. position and orientation of the device with respect to a 3D radiotherapy system) estimation for these devices. To compute 3D position for the target region, the intrinsic parameters (e.g. distance from an X-ray source to a detector and pixel pitch of the detector) of an imaging device must be provided. Intrinsic parameters of an imaging device may be obtained from the device specification sheets and on-site installation specs. However, intrinsic parameters are largely device dependent. For instance, the distance from an X-ray source to X-ray detector can change from device to device within a certain statistical range for the type of devices.

U.S. Patent Application Publication No. 2005/0180544 A1 (Sauer et al.) discloses a system and method for patient positioning for radiotherapy in the presence of respiratory motion. The method disclosed in '544 teaches using one or two X-ray imagers to acquire two sequences of the region that contains the target with an invasively implanted marker. If one X-ray imager is used, images are taken alternatively at two different angles (0° and 90°). The frequency of the image acquisition within a sequence is fixed and trigged by a respiratory monitoring device (noted that the fixed frequency mode may not be ideal because the organ motion caused by respiration is non-linear in nature in terms of 3D positions). After obtaining two sequences of X-ray images of the target region, method '544 teaches using the triangulation scheme to compute 3D coordinates of the target to form a 3D target position trajectory. The 3D target position trajectory enables radiation treatment with beam tracking or gating, thus allowing for motion compensation for all fields in which radiation doses are being delivered. In method '544, the 3D target position is also compared with a 4D target position data in a sequence of CT images to see if they match. If there is a significant change in the planned treatment, the treatment is stopped.

People skilled in the art understand that to effectively use the triangulation scheme, the intrinsic parameters of the X-ray imagers must be given, which is the same drawback that method '548 has. Noted also that method of '544 teaches manually or semi-automatically identifying targets in the captured images, which is not desirable in real-time irradiation adaptation.

The present invention is designed to overcome the problems set forth above.

SUMMARY OF THE INVENTION

Briefly, according to one aspect of the present invention, a method of target recognition for radiation therapy has a first target identification system for obtaining first target characteristics within a patient's body. A second target identification system for obtaining second target characteristics within the body is aided by the first target characteristics. Three-dimensional (3D) coordinates of the target region are calculated by a computation means with respect to a 3D radiotherapy system using the second target characteristics.

This invention builds on U.S. patent application Ser. No. 11/039,422, which discloses a method of real-time target detection in radiotherapy that solves the problem of detecting a target in a 2-D captured radiographic image in two ways:

1) The capture configuration for a radiograph at treatment time is based on an analysis of digitally reconstructed radiographs (DRR) that are generated from a CT planning image. This analysis determines capture conditions for which the target can be directly detected.
2) Powerful image processing techniques are used that enable target detection in the presence of superimposed anatomical structures.

This invention further builds on U.S. patent application Ser. No. 11/221,133, which discloses a method of identifying the region in a captured radiographic image that corresponds to the region of the target's projection in the image. This is accomplished by first, in the planning phase, determining processing conditions that result in the identification of the region of the target's projection in a DRR. A region is identified in the DRR by a method of image segmentation. The identified region is compared with the target's projection in this image. The segmentation process is optimized until the identified region and the target's projection are substantially the same. In the treatment phase, the optimized segmentation procedure is applied to a captured radiographic image in order to identify a region at or near the isocenter. Features of the region identified in the DRR are compared with those of the region identified in the captured radiographic image. Based on this comparison, the probability that the identified region in the captured radiographic image in the target is determined. This probability and the location of the identified region in the captured radiographic image are used to modify the delivery of therapeutic radiation.

This invention provides methods of target recognition and tracking without implanted fiducial markers for radiotherapy target confirmation. These methods essentially identify, in real-time, target characteristics including not only the morphological and spatial (3D physical location) information but also other features of the target. The method of target recognition mainly deals with measuring patient set-up (spatial and morphological) errors. The method of target tracking deals with target monitoring during the radiotherapy process.

The target morphological contour computation of the present invention is accomplished as following. In the planning phase, a volumetric target region is delineated from a volume image (CT) of the patient body. Without performing the reconstruction of a digitally reconstructed radiograph (DRR), the target contour in two-dimensional space can be calculated from the delineated volume surface of the target. This calculated contour is represented by a morphological descriptor that can be used to initialize the shape of a radiation collimator. In the treatment phase, the target region is identified (using the method disclosed in Ser. No. 11/221,133) and the region contour is represented by a morphological descriptor that is compared with the morphological descriptor generated in the planning phase, and can be used to redefine the shape of the radiation collimator. The morphological descriptor generated in the treatment phase can also be used in visual feedback display of target shape.

The target real-time three-dimensional physical location computation of the present invention facilitates measuring the set-up error between the isocenter and the target position in three directions (3D space).

The target real-time three-dimensional physical location computation of the present invention does not rely on knowing X-ray imagers' extrinsic parameters (e.g. position and orientation of the device with respect to a 3D radiotherapy system) and the intrinsic parameters (e.g. distance from an X-ray source to a detector and pixel pitch of the detector). This approach also does not require a perfect alignment of image planes of the X-ray imagers.

To accomplish the 3D computation, an adjustable phantom is devised to facilitate finding the 3D to 2D computational models of the X-ray imagers. These models assist the computation of the target real-time three-dimensional physical location. The adjustable phantom has markers that are detachable so that marker distribution patters are reconfigurable for different applications. The accurate physical locations of the markers are measured.

To obtain the 3D to 2D computational models of the X-ray imagers, the phantom is placed on the couch and two radiographs of the phantom are acquired with the X-ray imagers used in the treatment phase. The projections of the markers of the phantom are identified in the radiographs. The corresponding projections of the markers in two radiographs are established. The 3D to 2D computational models of the X-ray imagers then can be estimated by using the established corresponding projections of the markers and the measured physical locations of the markers.

In the treatment phase, with the same X-ray imagers, two radiographs of the patient body are captured. Using the algorithms devised in Ser. No. 11/221,133, target regions in the two radiographs can be identified.

Corresponding feature points such as region centroids in the two target regions in the two radiographs are then computed. Physical 3D locations of the corresponding feature points are subsequently calculated using the 3D to 2D computational models of the X-ray imagers. The computed physical 3D locations are used to represent the target location in 3D space for confirmation.

The method of target tracking during a bodily process of the present invention identifies target characteristics in the projective radiographs in the treatment phase is aided by the identified target characteristics in the planning phase at the beginning of the tracking process. The subsequent target characteristics tracking is aided by the previously identified target characteristics in the treatment phase. Radiographic data collection (radiograph acquisition) for target characteristics identification is regulated according to the target motion nonlinear property. The data collection is initiated and terminated by a device that monitors a bodily process (e.g. respiration).

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DETAILED DESCRIPTION OF THE INVENTION

Figure 1:
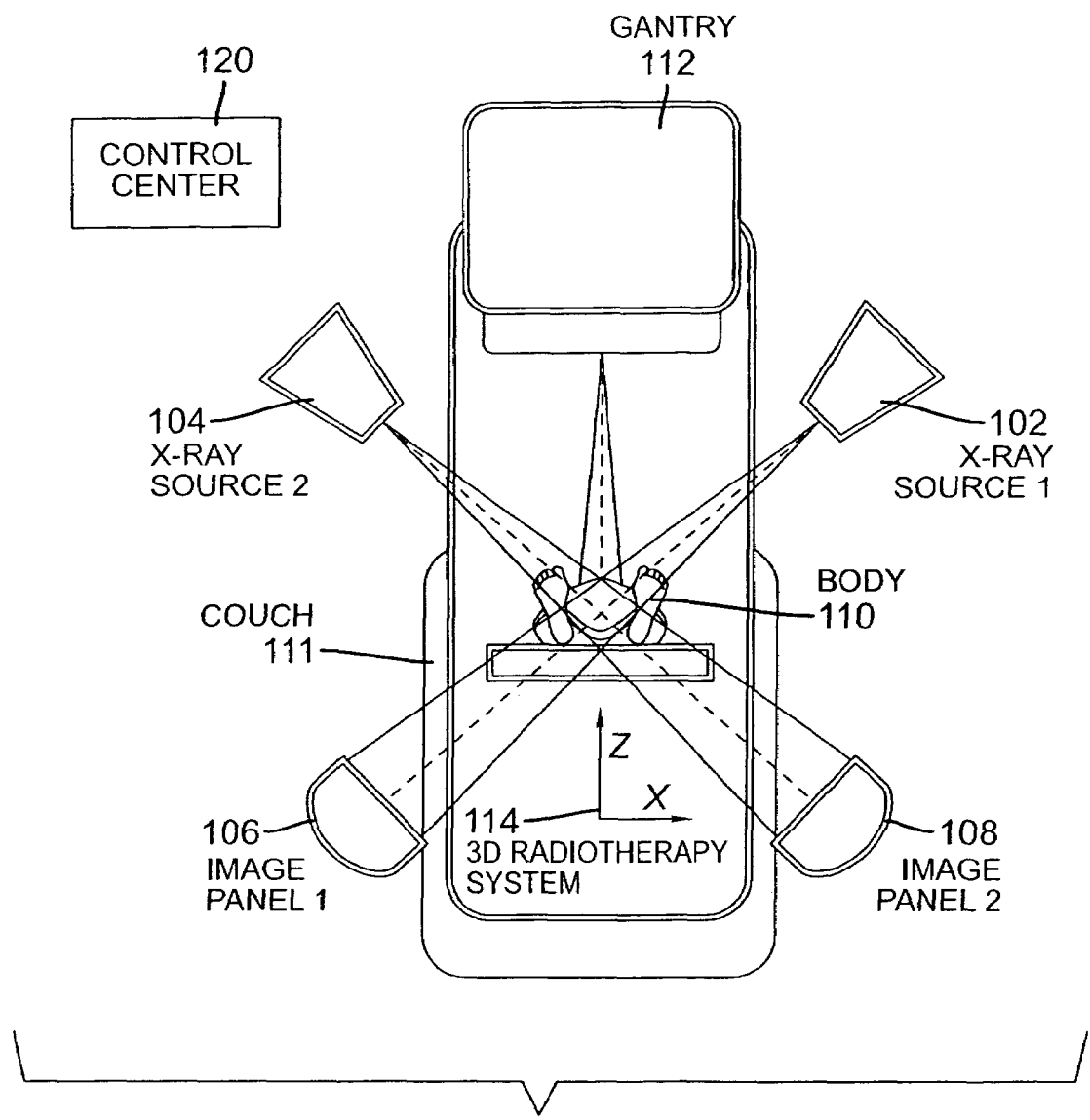
FIG. 1 is an illustration of a configuration of adjustable projective imaging devices of a second target identification system together with a radiation therapy equipment for target confirmation according to an exemplary embodiment of the current invention.

The following is a detailed description of the preferred embodiments of the invention, reference being made to the drawings in which the same reference numerals identify the same elements of structure in each of the several figures.

FIG. 1 depicts a configuration of projective imaging devices of the second target identification system together with a radiation therapy equipment for target confirmation according to an exemplary embodiment of the current invention, including exemplary X-ray imaging source 1 (102), X-ray imaging source 2 (104), image panel 1 (106), image panel 2 (108), body 110, couch 111, gantry 112, three-dimensional radiotherapy system (3D coordinate system) 114 and control center 120.

The gantry 112 includes a radiation beam source such as a linear accelerator that is positioned to irradiate a target in body 110 located on couch 111. The imaging X-ray sources 1 (102) and 2 (104) can be mounted on ceilings. Alternatively, the X-ray imaging sources 1 (102) and 2 (104) can be mounted on fixtures that are attached to the gantry 112. The X-ray image sources 1 and 2 may be oriented differently from what shown in FIG. 1. The X-rays for imaging sources 1 (102) and 2 (104) are in the diagnostic KeV range for maximizing the detectability of the target. The image panels 1 (106) and 2 (108) may be full-field direct detector arrays such as Kodak DR 9000 with an active area of 14×17 inch and a 139-μm detector element pitch. The image panels 1 (106) and 2 (108) are installed opposite to the image sources and in such a way that enough clearance exists in order to avoid a collision with the gantry when the gantry rotates around the radiation isocenter.

The radiation equipment may include an exemplary verification X-ray flat panel detector (not shown) installed underneath the couch 111 for high-energy (MeV) radiotherapy beam dose verification. By using the verification X-ray flat panel detector, an alternative configuration (not shown) of the projective imaging devices of the second target identification system can be realized. Instead of using separate image panels, X-ray sources 1 and 2 may time-share the verification X-ray flat panel detector to simplify the system.

Figure 2:
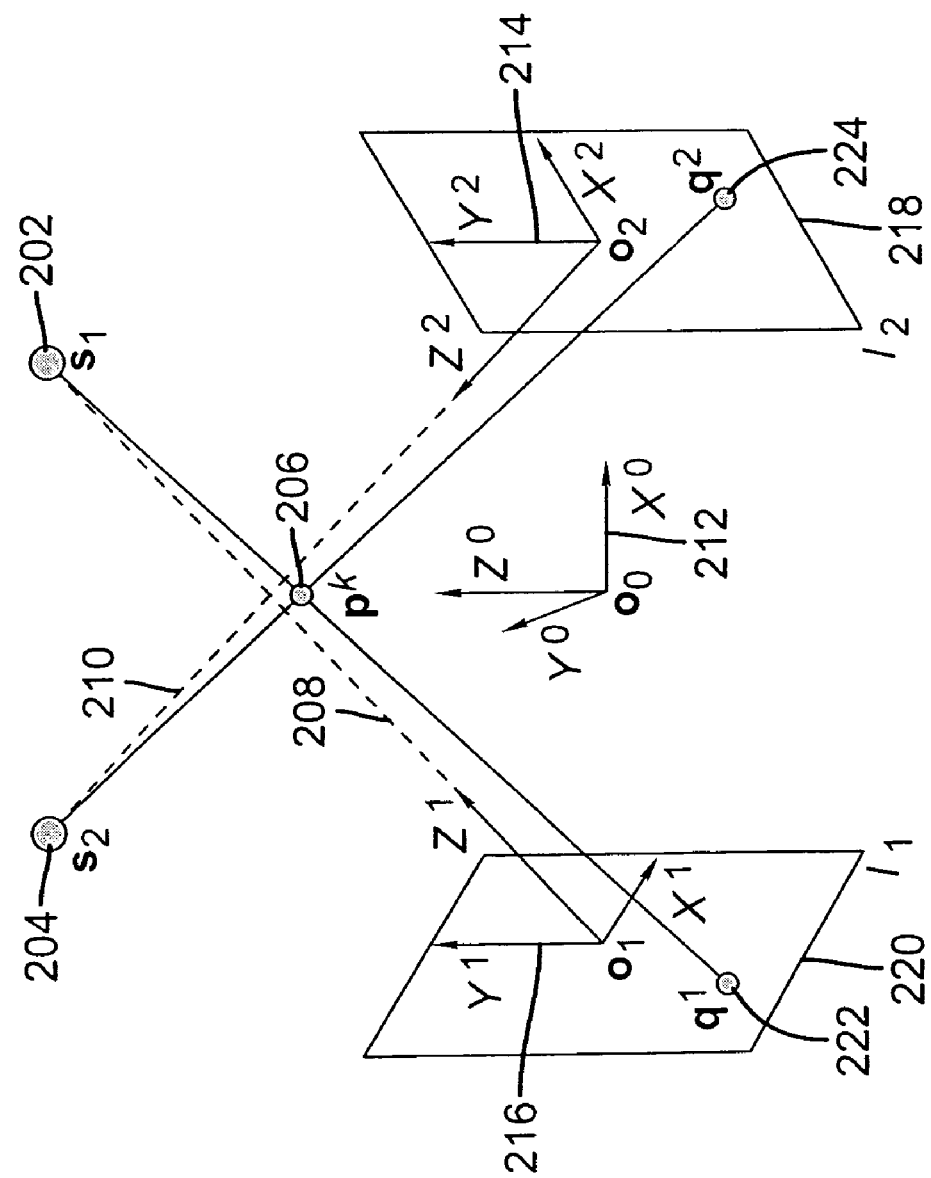
FIG. 2 is an illustration of perspective projection structure of the projective imaging devices of the second target identification system according to the adjustable projective imaging configuration.

FIG. 2 is a supplement to FIG. 1 illustrating perspective projection structure of the projective imaging devices of the second target identification system shown in FIG. 1, including a 3D world (radiotherapy) system 212 (also 114) denoted by $(X^0, Y^0, Z^0)$, a 3D local coordinate system 216, denoted by $(X^1, Y^1, Z^1)$, associated with X-ray $s_1$ (202, also 102), a 3D local coordinate system 214, denoted by $(X^2, Y^2, Z^2)$, associated with X-ray $s_2$ (204, also 104). Without loss of generality, the origin, $o_1$, of $(X^1, Y^1, Z^1)$ is set at the center of an image plane $I_1$ (220, also 106), the origin, $o_2$, of $(X^2, Y^2, Z^2)$ is set at the center of an image plane $I_2$ (218, also 108), and the origin, $o_0$, of $(X^0, Y^0, Z^0)$ is set arbitrarily between $o_1$, and $o_2$. Imaging sources $s_1$ (202) and $s_2$ (204) are modeled as pinhole X-ray cameras. The perspective projection structure of the projective imaging system shown in FIG. 2 are to be used in deriving 3D to 2D computational models of projective imaging devices of the second target identification system later.

The control center 120 may include electronic and mechanical units used for controlling couch position, gantry rotation, X-ray imaging device position and orientation, and other devices such as in vitro respiration monitoring unit (not shown). It may also include signal and image processing, graphic user interface and input/output devices that are useful in various procedures described next.

Figure 3A:
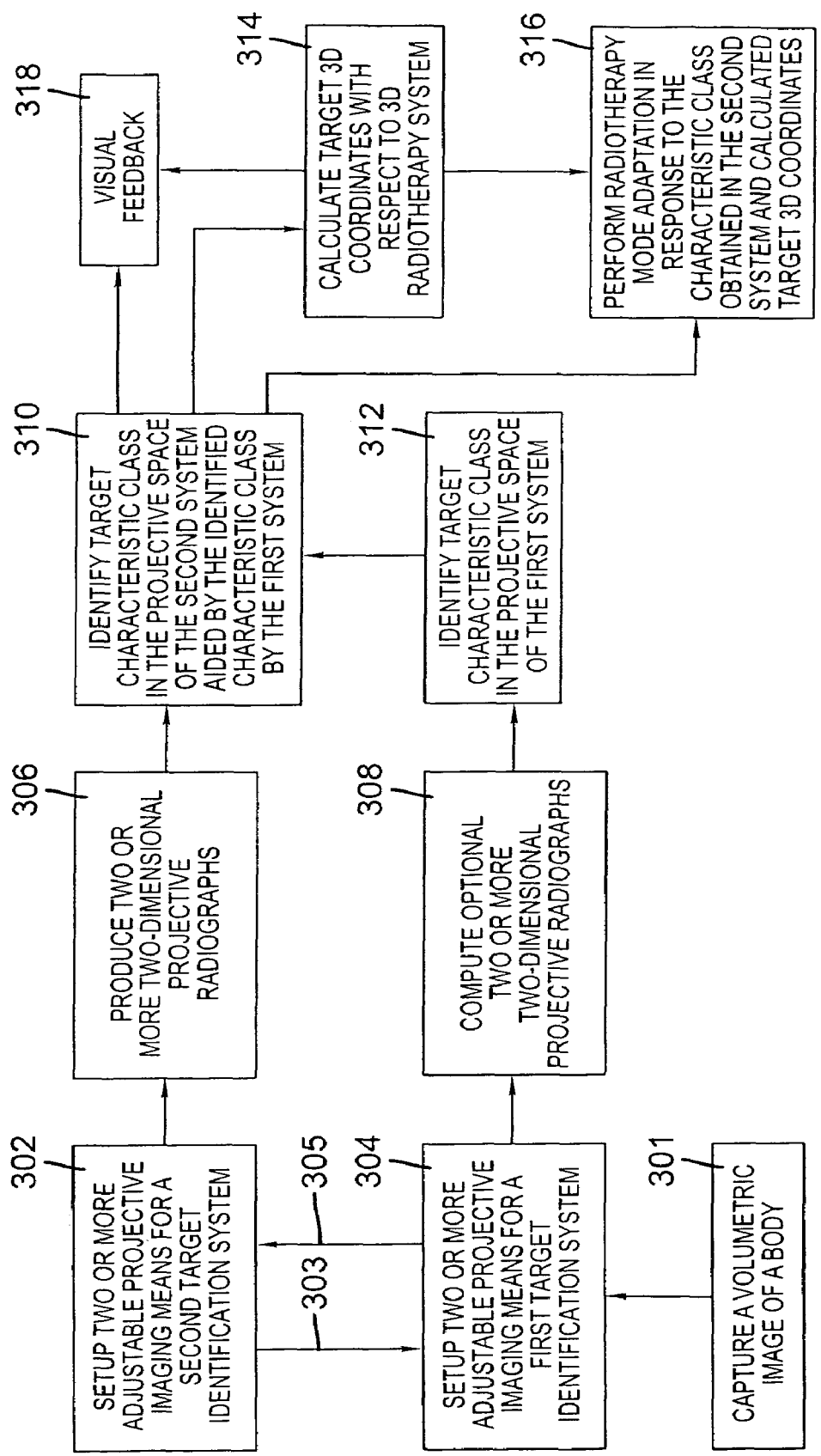
FIG. 3A is a flowchart illustrating the method of target recognition for radiotherapy according to an exemplary embodiment of the current invention.
Figure 3B:
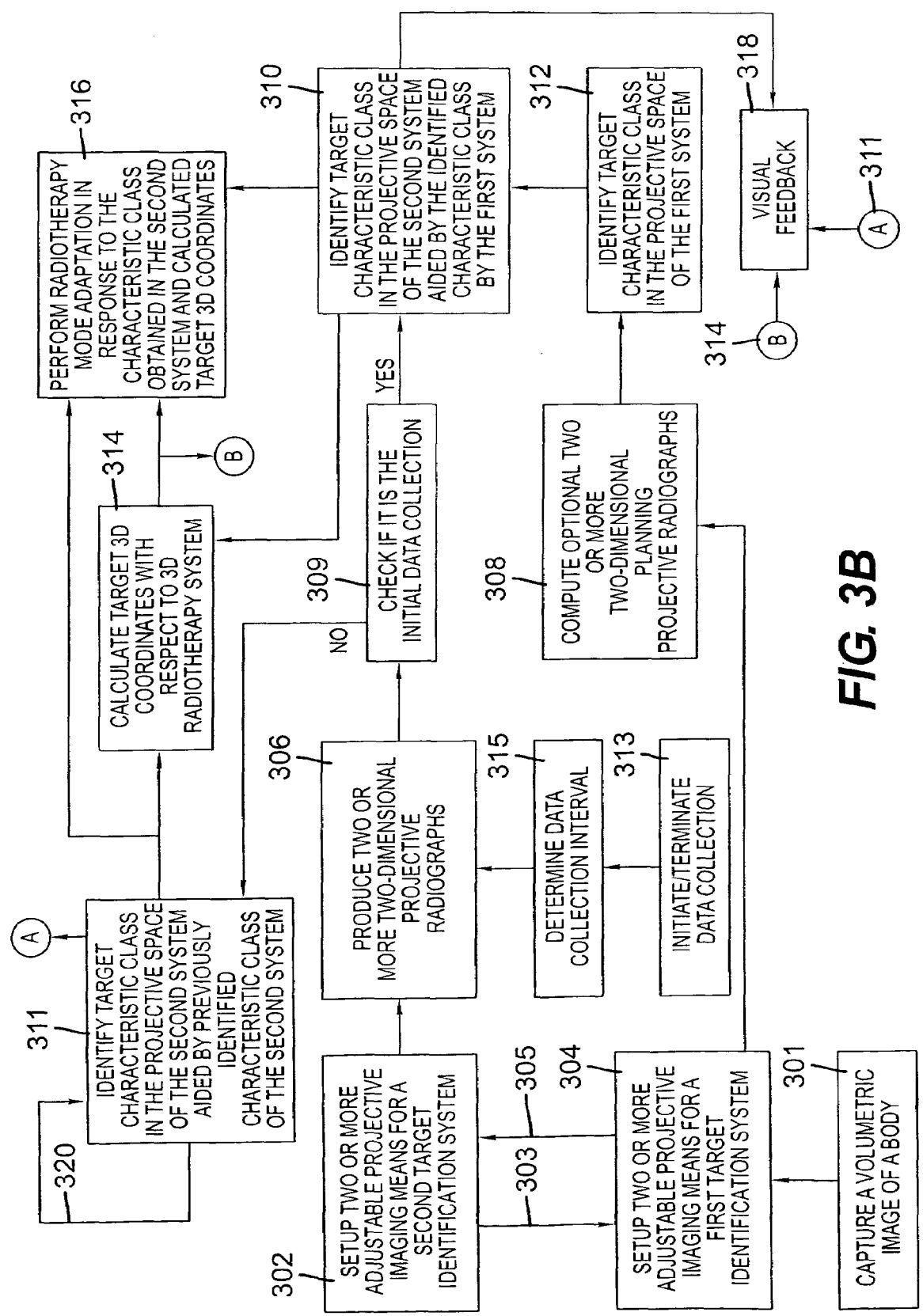
FIG. 3B is a flowchart illustrating the method of target tracking for radiotherapy according to an exemplary embodiment of the current invention.

Turning now to FIGS. 3A and 3B, the methods of the present invention will be described. FIG. 3A is a flow chart illustrating one embodiment of the method for target recognition for radiotherapy of the present invention. Prior to radiotherapy treatment, a volumetric image of the patient body is captured in step 301. From the volumetric image, a volumetric target can be delineated manually with the help of image processing tools. Volumetric images are usually CT or MRI scans. A volumetric image of the target is useful especially in conformal radiotherapy that is most beneficial to the patient for targets that are close to important organs and structures in the body. With the conformal radiotherapy, less healthy tissue is included in the radiotherapy field because metal blocks are put in the path of the radiation beam to change the shape of the beam so that it conforms more closely to the shape of the target.

The volumetric image also plays a role in patient position verification. Conventionally, to transfer target location information from cross-sectional computed tomographic (CT) scans or magnetic resonance images to the simulation and verification portal images used in planning radiotherapy, radio-opaque markers attached to the patient are used as reference points. The target and any desired normal structures are then outlined manually on each CT section by a radiologist.

An embodiment of target recognition method of the present invention is detailed next.

Figure 4:
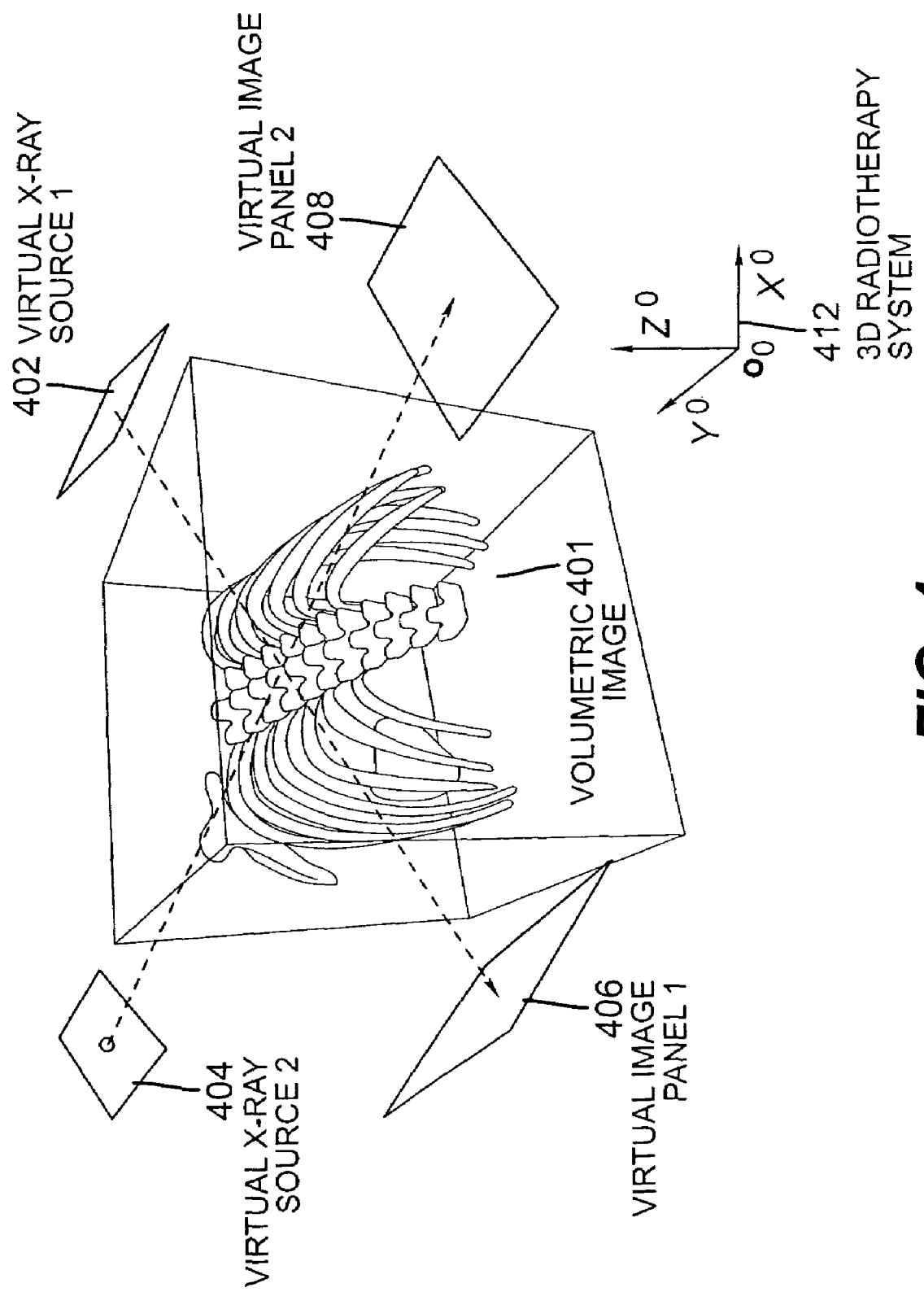
FIG. 4 is an illustration of adjustable projective imaging devices of a first target identification system according to an exemplary embodiment of the current invention.

The volumetric image of the body obtained in step 301 contains three-dimensional target region information that is to be transformed (projected) to two-dimensional space. An exemplary setup 302 for transforming (projecting) information from 3D volumetric data to 2D space is depicted in FIG. 4. A volumetric image 401 is placed in a three-dimensional space 412 as if it is placed on the couch 111. In FIG. 4, two exemplary virtual X-ray pairs, X-ray source 1 (402) and panel 1 (406), and X-ray source 2 (404) and panel 2 (408) are the adjustable projective imaging devices for a first target identification system. These two projective imaging devices are optimally positioned and oriented so that overlap of normal anatomy with the target is minimized and the boundary of the target is distinct in the 2D image panels 406 and 408 (see the embodiment of the method of radiation therapy with target detection in the co-pending U.S. patent application Ser. No. 11/039,422).

The position and. orientation information of the virtual X-ray imagers obtained in step 304 is input (arrow 305) to step 302 to adjust the position and orientation of two exemplary adjustable projective imaging devices, X-ray pairs 102-106 and 104-108, for the second target identification system.

This adjustment of the position and orientation of X-ray pairs 102-106 and 104-108 results in two X-ray radiographs (106 and 108) that contain, in theory, the same contents appeared in two virtual images (406 and 408) if the same body that is volumetrically imaged is placed on the couch. This facilitates using information gathered in the first target identification system to recognize the target in the second target identification system.

An alternative approach of the present invention to setting up the projective imaging devices of the first target identification system and that of the second target identification system is to use (arrow 303) the position and orientation information of X-ray pairs 102-106 and 104-108 in step 304 to adjust the position and orientation of the virtual X-ray pairs 402-406 and 404-408. As revealed in the co-pending U.S. patent application Ser. No. 11/039,422, the measuring position and orientation of X-ray pairs 102-106 and 104-108 can be accomplished, for example, with the use of markers that are detected by digital cameras or by any other means of measuring position and orientation.

Figure 8A:
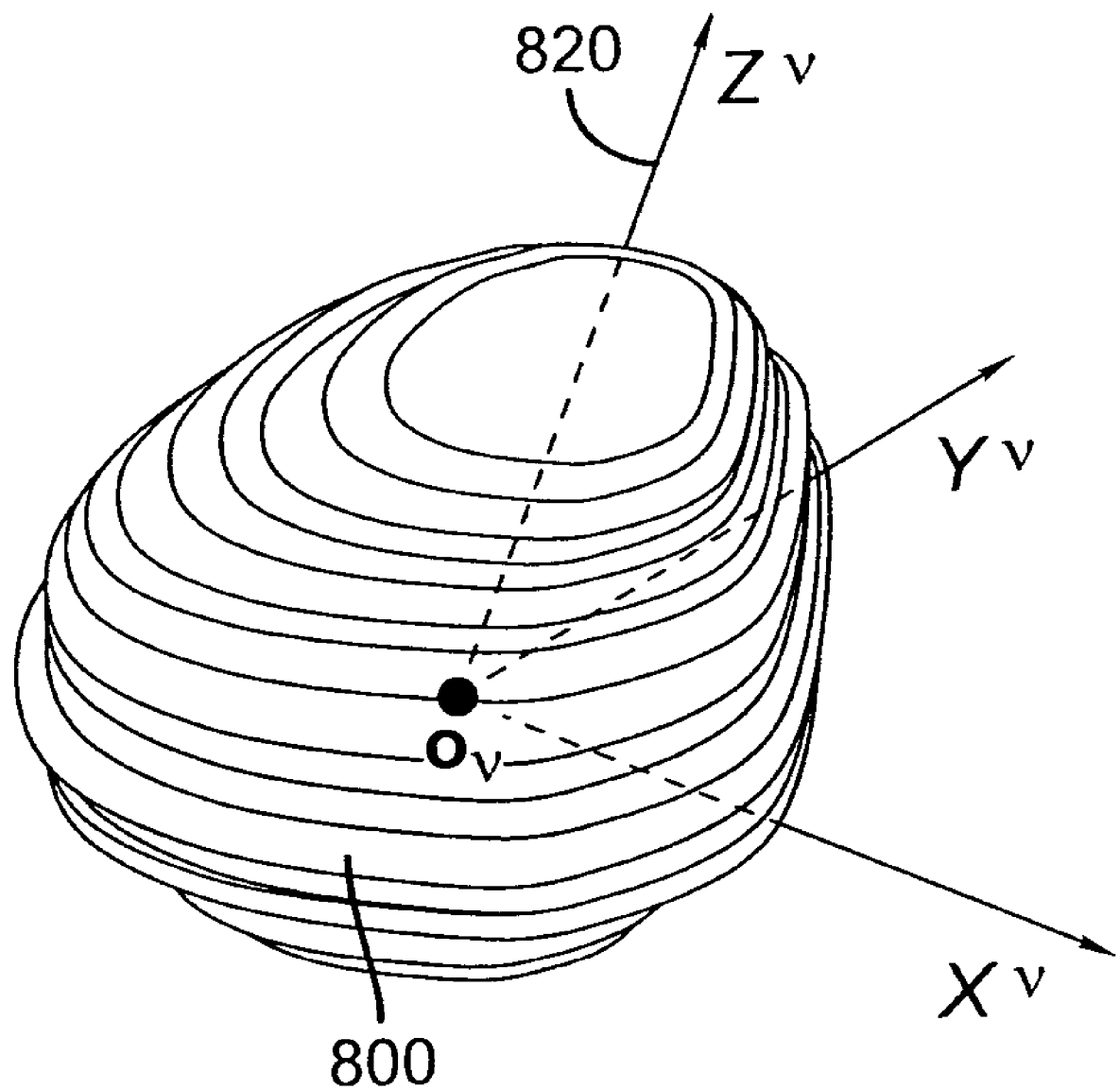
FIG. 8A is an illustration of a volumetric image of a target according to an exemplary embodiment of the current invention.

After the calibration (setup) of the projective imaging devices of the first target identification system and that of the second target identification system, the volumetric target region is ready to be transformed (projected) to two-dimensional space to facilitate target recognition in the second target identification system. FIG. 8A illustrates an exemplary target volume 800 whose boundary is delineated by the radiologist. With the known boundary position in the volumetric image and the measurement of the position and the orientation of the projective imaging devices of the first target identification system, the projections of the target volume 800 can be readily computed through projective geometry. In practice, it may project just a partial volume that contains the target region and related volumes along the projection path onto the 2D projective radiograph space (step 308). These two projective radiographs are used in step 312 to identify target characteristics.

Note that it is not necessary to perform volume projection if only the target contour in two-dimensional space is needed. The target contour can be easily calculated from the delineated volume surface of the target without performing the reconstruction of a digitally reconstructed radiograph (DRR). An exemplary calculation of the target contour is briefly explained next.

Define a local target 3D coordinate system $(X^v, Y^v, Z^v)$ 820 whose axes are parallel to that of a projective imaging device of the first system. Denote the delineated volume surface 800 by $V(x^v, y^v, z^v)$ in said coordinate system $(X^v, Y^v, Z^v)$ 820. Note that the axes of coordinate system $(X^v, Y^v, Z^v)$ 820 are in parallel to that of one of the local three-dimensional coordinate systems of the projective imaging devices $(X^1, Y^1, Z^1)$ or $(X^2, Y^2, Z^2)$ at a time. The origin, $o^v$, of the system $(X^v, Y^v, Z^v)$ can be arbitrarily placed inside or outside the volume 800.

Figure 8B:
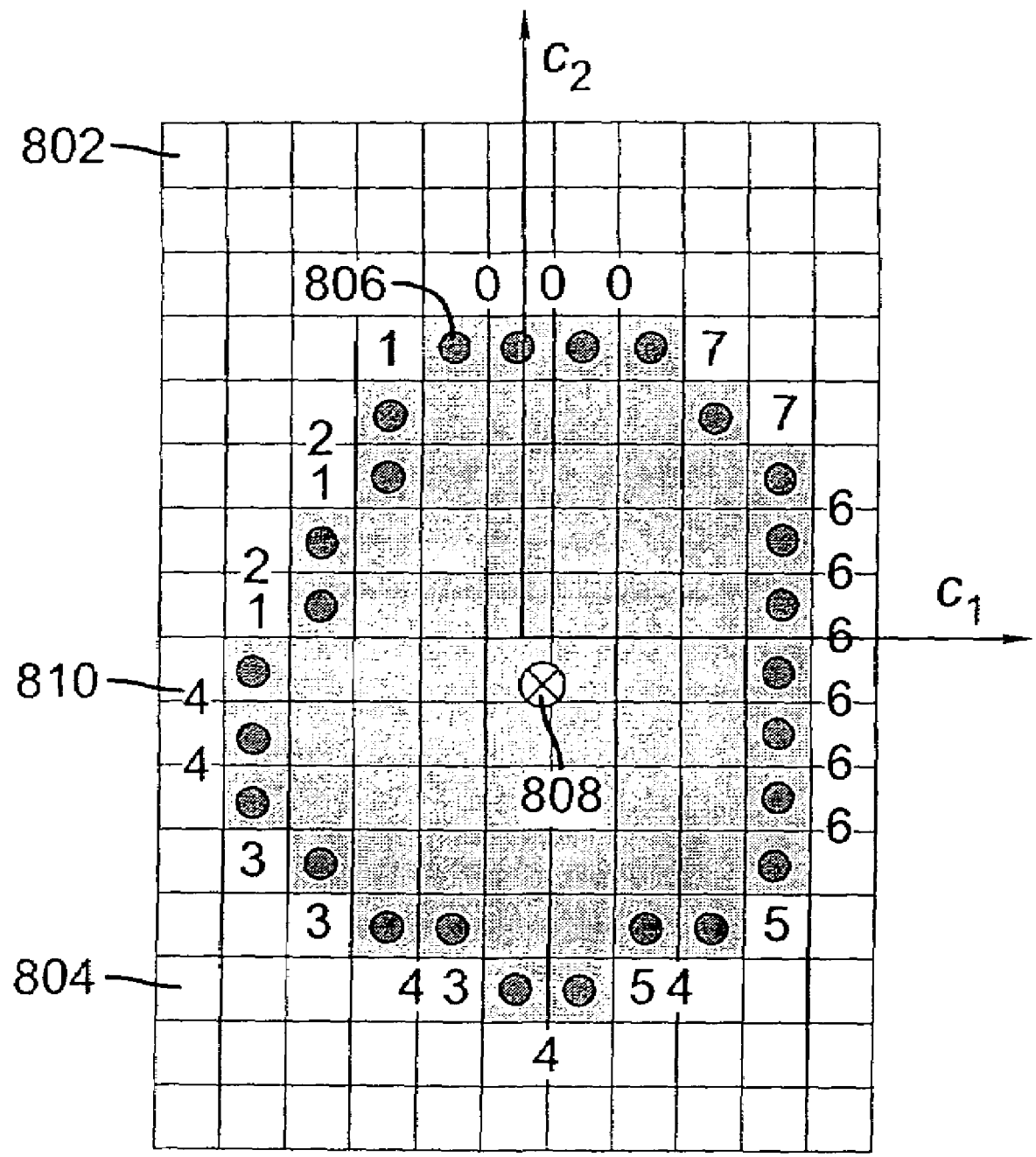
FIG. 8B is a graphics display of a projection of a volumetric image of a target and parameters of the projection according to an exemplary embodiment of the current invention.
Figure 8C:
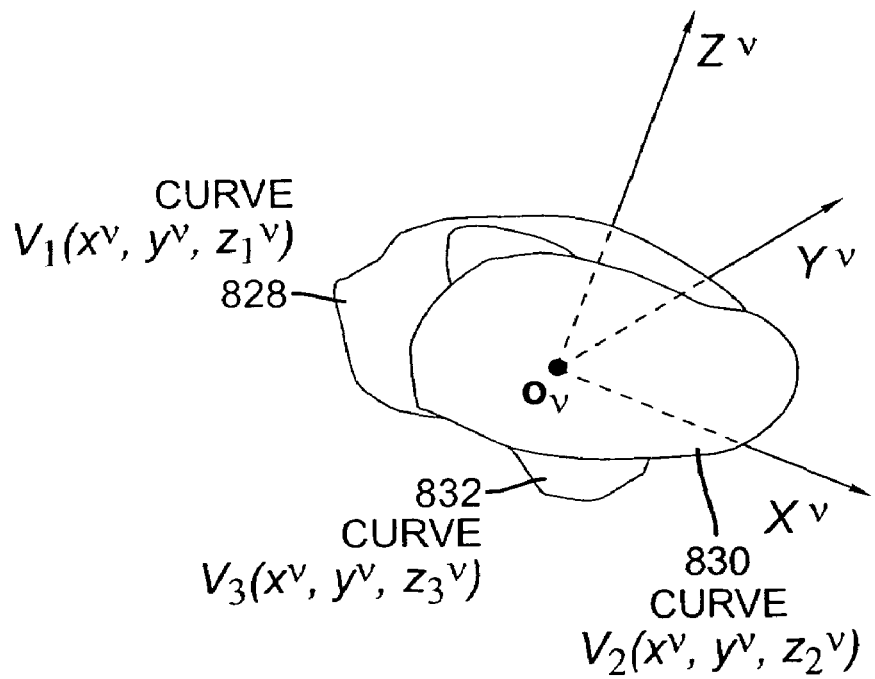
FIG. 8C is an illustration of curves of a surface of the volumetric image of a target according to an exemplary embodiment of the current invention.

It is obvious that at a certain height $z_n^v$ the expression $V_n(x^v, y^v, z_n^v)$ represents a surface curve of the delineated target volume surface in a plane that is parallel to the projection plane of the projective imaging device of the first system, where $z_n^v$ is a constant. Exemplarily curves are shown in FIG. 8C as $V_1(x^v, y^v, z_1^v)$ (828), $V_2(x^v, y^v, z_2^v)$ (830), and $V_3(x^v, y^v, z_3^v)$ (832).

The calculation of the tumor contour starts by collapsing, in the $z^v$ direction, all the surface curves $V_n(x^v, y^v, z_n^v)$ into a common two-dimensional plane of $z_n^v = n$ that is parallel to the projection plane of the projective imaging device of the first system. Note that $z^v$ direction is perpendicular to said plane.

Figure 8D:
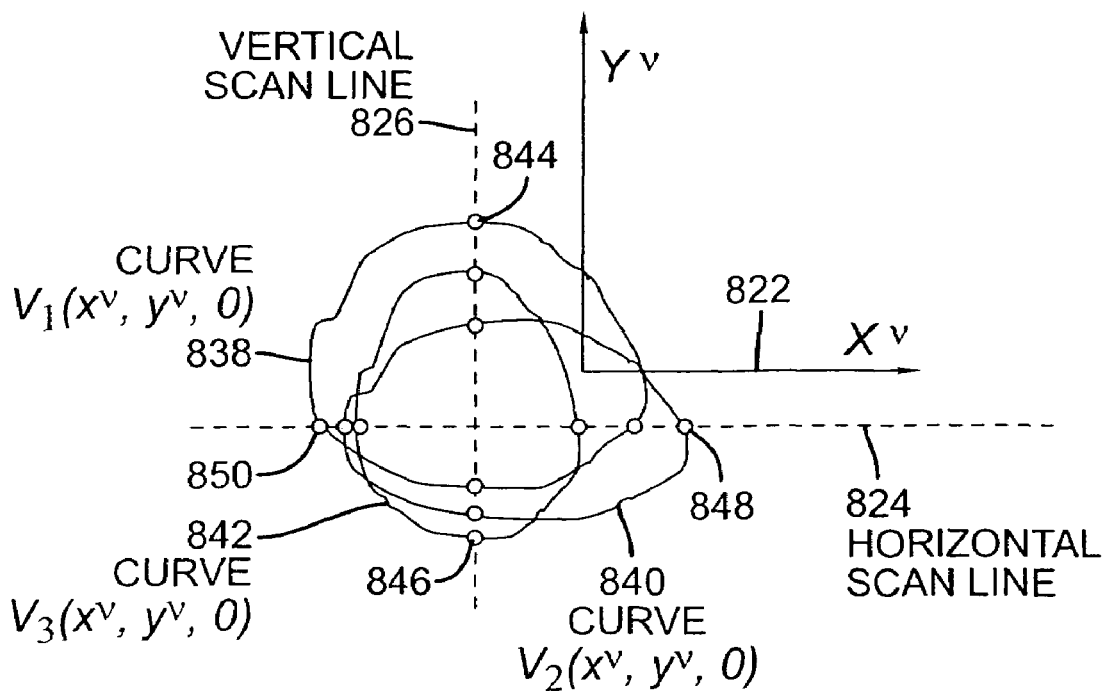
FIG. 8D is an illustration of scanning the collapsed curves of a surface of the volumetric image of a target according to an exemplary embodiment of the current invention.

As is shown in FIG. 8D, an exemplary common plane is the $(X^v, Y^v)$ plane (822) of the coordinate system $(X^v, Y^v, Z^v)$ (820), that is, $z_n^v = 0$. After collapsing the original curves, three new curves $V_1(x^v, y^v, 0)$ (838), $V_2(x^v, y^v, 0)$ (840), and $V_3(x^v, y^v, 0)$ (842) appear in the $(X^v, Y^v)$ plane.

The calculation process then performs vertical and horizontal scans across the plane. An exemplary vertical scan line 826 intersects with the three exemplary curves six times. The outmost intersection points 844 and 846 on this exemplary scan line are saved to a contour point list. An exemplary horizontal scan line 824 intersects with the curves six times. The outmost intersection points 848 and 850 on this exemplary scan line are collected and saved to the contour points list. The calculated contour points are represented by a morphological descriptor that can be used to initialize the shape of a radiation collimator.

In a normal radiograph or in a DRR, the contour finding is accomplished by separating projection of the target volume and the projection of the neighboring voxels with the method disclosed in the co-pending U.S. patent application Ser. No. 11/221,133.

For convenience, denote the target characteristics by a symbol C that contains data members of features, position (spatial parameter), descriptor (morphological parameter), functions functions, and metadata metadata.

Member C.features describes region area, statistics, gradient, texture, surface etc. The method of extraction of C.features is revealed in the co-pending U.S. patent application Ser. No. 11/221,133. Exemplary C.functions are image and computer vision operations such as classification, segmentation, and registration. Exemplary C.metadata are the time when the target processed and device specs.

An exemplary C.position is a centroid of the target region that describes the region gravity center and can be readily computed. FIG. 8B illustrates the projection 802 of the target volume and its immediate neighboring voxels. Projection 802 may be generated by one of the virtual X-ray imagers, for instance, virtual X-ray imager pair 402-406. Each grid 804 represents a pixel in projection 802. The gray area is the projection of the target volume, the white area is the projection of the neighboring voxels.

Denote the coordinate system of projection 802 by $(c_1, c_2)$; the origin of the coordinate system is at the center of the projection 802 as shown in FIG. 8B. The C.position 808 of the exemplary target projection is then computed as $$C.position.c_1 = m_{10}/m_{00}$$

$$C.position.c_2 = m_{01}/m_{00}$$

where $C.position.c_1$ is the coordinate of C.position in the horizontal direction and $C.position.c_2$ is the coordinate of C.position in the vertical direction, and the moments are computed as:

$$m_{pq} = \int_{-\infty}^{\infty}\int_{-\infty}^{\infty} c_1^p c_2^q f(c_1, c_2) dc_1 dc_2$$

where $f(c_1,c_2)=1$ in the gray area and 0 otherwise in this application.

Member C.descriptor describes the contour of the projection of the target volume that is highlighted by black dots in FIG. 8B. An exemplary representation of C.descriptor is the well-known chaincode (see http://www.bmva.ac.uk/bmvc/1997/papers/062/node2.html) in computer vision and pattern recognition. In FIG. 8B, the chaincode (e.g. 4 (810)) is shown next to the contour. Choosing a start point 806, the representation of the contour will be C.descriptor=00077666666545434334412121.

Noted that steps 302 and 304 assure that radiographs generated in step 306 will match the radiographs produced in step 308. Therefore, if the same body that is used in step 301 is placed in the projective path of X-ray pairs 102-106 or 104-108, the same projection of the target region should be expected in the radiographs obtained in step 306. However, in practice, this rarely happens due to various reasons. The target characteristics C obtained in the first target identification system is therefore served as an aid to identify target characteristics in the second target identification system in step 310 after acquiring projective radiographs with X-ray imager pairs 102-106 and 104-108 in step 306. For instance, functions and their associated parameters used in the first target identification system are employed in the second target identification system with or without modifications. Spatial and morphological parameters identified in the first target identification system are used as initiation parameters in the second target identification system. Features derived in the first target identification system are compared with that derived in the second target identification system.

Noted that steps 304, 308 and 312 constitute a first target identification system for obtaining target characteristics of a target region within a body; steps 302, 306 and 310 constitute a second target identification system for obtaining target characteristics of a target region within the body. It is also understood that steps 302, 303, 304 and 305 provide a calibration means for the first and second target identification systems.

An exemplary of a first target identification system is a planning target identification system in a planning phase for the radiotherapy. The first target identification system (or the first system for short) and the planning target identification system (or the planning system for short) are used interchangeably in the following discussions.

An exemplary of a second target identification system is a treatment real-time target identification system in a treatment phase for the radiotherapy. The second target identification system (or the second system for short) and the treatment real-time target identification system (or treatment system for short) are used interchangeably in the following discussions.

In step 310, target characteristics $C^1$ and $C^2$ are generated with the two radiographs (from image panel 1 (106, also 220) and image panel 2 (108, also 218)). Their members $C^1$.position and $C^2$.position are used in step 314 to calculate target 3D coordinates with respect to 3D radiotherapy system 114 (also 212).

A preferred method of calculating 3D coordinates of a physical point from its 2D projections of the present invention is to implicitly use intrinsic and extrinsic parameters of the projective imaging devices. To do so, the relationship between the three-dimensional space and two-dimensional projection space need to be found. That is equivalent to computing a 3D to 2D computational model for a projective imaging device with respect to a three-dimensional coordinate system. The process of finding the 3D to 2D computational model and using the model to calculate 3D coordinates of a physical point from its 2D projections is elaborated next.

Denote a three-dimensional physical point (206 in FIG. 2) with respect to 3D coordinate systems 212, 214 and 216 by homogeneous representations $\tilde{p}^k = [x_p^k\ y_p^k\ z_p^k\ 1]^T$; k=0,1,2, and its associated projections (222 and 224) by homogeneous vectors $\tilde{q}^m = [wx_q^m\ wy_q^m\ 0\ w]^T$; m=1,2, where w is a scaling factor.

Noted that coordinate system 216 is a local 3D coordinate system with its $(X^1,Y^1)$ plane aligned with the 2D coordinate system of image plane $I_1(218)$, and coordinate system 214 is a local 3D coordinate system with its $(X^2,Y^2)$ plane aligned with the 2D coordinate system of image plane $I_2(218)$. The coordinate system 212 is a world 3D coordinate system.

It is readily to verify that the projections of the physical point 206 in the coordinate systems associated with the X-ray imaging systems (202-220 and 204-218) can be computed as $$\tilde{q}^m = F_0^m \tilde{p}^m; m = 1, 2;\qquad(1)$$

where $$F_0^m = \begin{bmatrix} 1 & 0 & 0 & 0 \\ 0 & 1 & 0 & 0 \\ 0 & 0 & 0 & 0 \\ 0 & 0 & -1/d^m & 1 \end{bmatrix}; m = 1, 2;$$

and $d^m$ is the distance between the X-Ray source $s_m$ and the origin $o_m$. Noted that the line (208 or 210) $\overline{s_m o_m}$ is perpendicular to the image plane $I_m$ (220 or 218) and aligns with axis $Z^m$, m=1,2. Noted also that in Equation (1), the three-dimensional point 206 is represented by $\tilde{p}^m$ in local three-dimensional coordinate systems (216 and 214). To express the projections (222 and 224) in terms of the world coordinate representation $\tilde{p}^0$, a coordinate transformation operation is applied as $$\tilde{p}^m = \prod_{i=1}^{4} F_i^m \tilde{p}^0; m = 1, 2,\qquad(2)$$

where $\Pi$ is a matrix product operator.

In the above expression, $F_1^m$ performs a rotational transformation around the $Z^0$ axis, $F_2^m$ performs a rotational transformation around the $Y^0$ axis, and $F_3^m$ performs a rotational transformation around the $X^0$ axis. $F_4^m$ performs a translational transformation with respect to origin o along $X^0, Y^0$ and $Z^0$ axes.

Substituting Equation (2) to Equation (1) yields $$\tilde{q}^m = \prod_{i=0}^{4} F_i^m \tilde{p}^0; \, m = 1, 2;  \quad (3)$$

In fact, vector $\tilde{q}^m$ can be shortened as $\tilde{q}^m = [wx_q^m \, wy_q^m \, w]^T$, and all the transformation matrices $F_i^m$ can be grouped together to become a single matrix $A_m$. It then yields $$\tilde{q}^m = A_m \tilde{p}^0;  \quad (4)$$

where $A_m = [a_{ij}^m]$; $i \in [1,2,3]$, $j \in [1,2,3,4]$ that defines the 3D to 2D computational model which is to be estimated with a preferred method described next.

With N, (N≧6), known non-coplanar 3D points $\{p_1^0, \ldots p_n^0, \ldots p_N^0\}$ and their corresponding projections $\{q_1^1, \ldots q_n^1, \ldots q_N^1\}$ and $\{q_1^2, \ldots q_n^2, \ldots q_N^2\}$, where $p^0 = [x_p^k \, y_p^k \, z_p^k]^T$ and $q_n^m = [x_{q_n}^m \, y_{q_n}^m]^T$, the twelve unknown variables, $a_{ij}^m$; $i \in [1,2,3]$, $j \in [1,2,3,4]$, of matrix $A_m$ can be solved for each of the X-ray cameras (m=1,2).

In practice, set $a_{34}^m = 1$. Denote the rest eleven variables by $a^m = [a_{11}^m \, a_{12}^m \, a_{13}^m \, a_{14}^m \, a_{21}^m \, a_{22}^m \, a_{23}^m \, a_{24}^m \, a_{31}^m \, a_{32}^m \, a_{33}^m]^T$. The solution of $a^m$ will be in the form of $$a^m = ((B^m)^T B^m)^{-1} (B^m)^T r^m  \quad (5)$$

where $$r^m = [(q_1^m)^T, \ldots, (q_N^m)^T]^T \text{ and}$$

$$B^m = \begin{bmatrix} (\tilde{p}_1^0)^T & 0 & -x_{q_1}^m (p_1^0)^T \\ 0 & (\tilde{p}_1^0)^T & -y_{q_1}^m (p_1^0)^T \\ \vdots & \vdots & \vdots \\ (\tilde{p}_N^0)^T & 0 & -x_{q_N}^m (p_N^0)^T \\ 0 & (\tilde{p}_N^0)^T & -y_{q_N}^m (p_N^0)^T \end{bmatrix};$$

where $0 = [0 \, 0 \, 0 \, 0]$ and $m = 1, 2$.

After having estimated the 3D to 2D computational models for the two projective imaging devices, the 3D coordinates of an unknown physical point, for example $p^0$ (206), can be calculated by using its projections ($q^1$ (222) and $q^2$ (224)) and the computational models $A_m$, which is formularized below.

Returning back to Equation (4), by eliminating the scale factor wand rearranging the variables, Equation (4) can be re-written in a matrix operation form of $$Mp^0 = N;  \quad (6)$$

where $$M = \begin{bmatrix} M^1 \\ M^2 \end{bmatrix}; \text{ and } M^m = \begin{bmatrix} a_{1j}^m \\ a_{2j}^m \end{bmatrix} - \begin{bmatrix} a_{3j}^m \\ a_{3j}^m \end{bmatrix} q^m;$$

the column index j=1,2,3, and m=1,2;

$p^0 = [x_p^0 \, y_p^0 \, z_p^0]^T$;

$N = [N^1 \, N^2]^T$; where $N^m = a_{34}^m (q^m)^T - [a_{i4}^m]^T$; the row index i=1,2, and m=1,2.

The 3D coordinates of an unknown physical point $p^0$ can be optimally calculated with respect to the world coordinate system $(X^0, Y^0, Z^0)$ as $$p^0 = (M^T M)^{-1} M^T N.  \quad (7)$$

Figure 6:
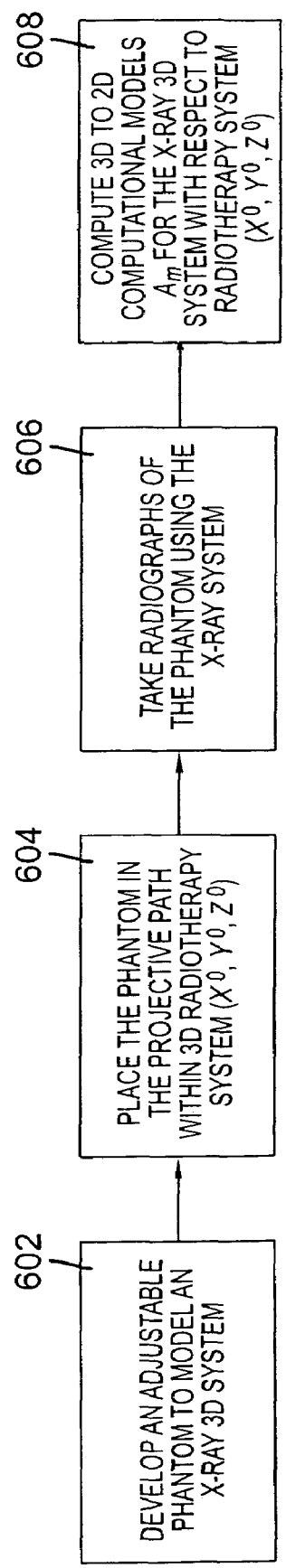
FIG. 6 is a flowchart illustrating the method of computing computational models of the projective imaging devices of the second target identification system according to an exemplary embodiment of the current invention.

The above procedures for computational model estimation are illustrated in the flowchart in FIG. 6.

Figure 5:
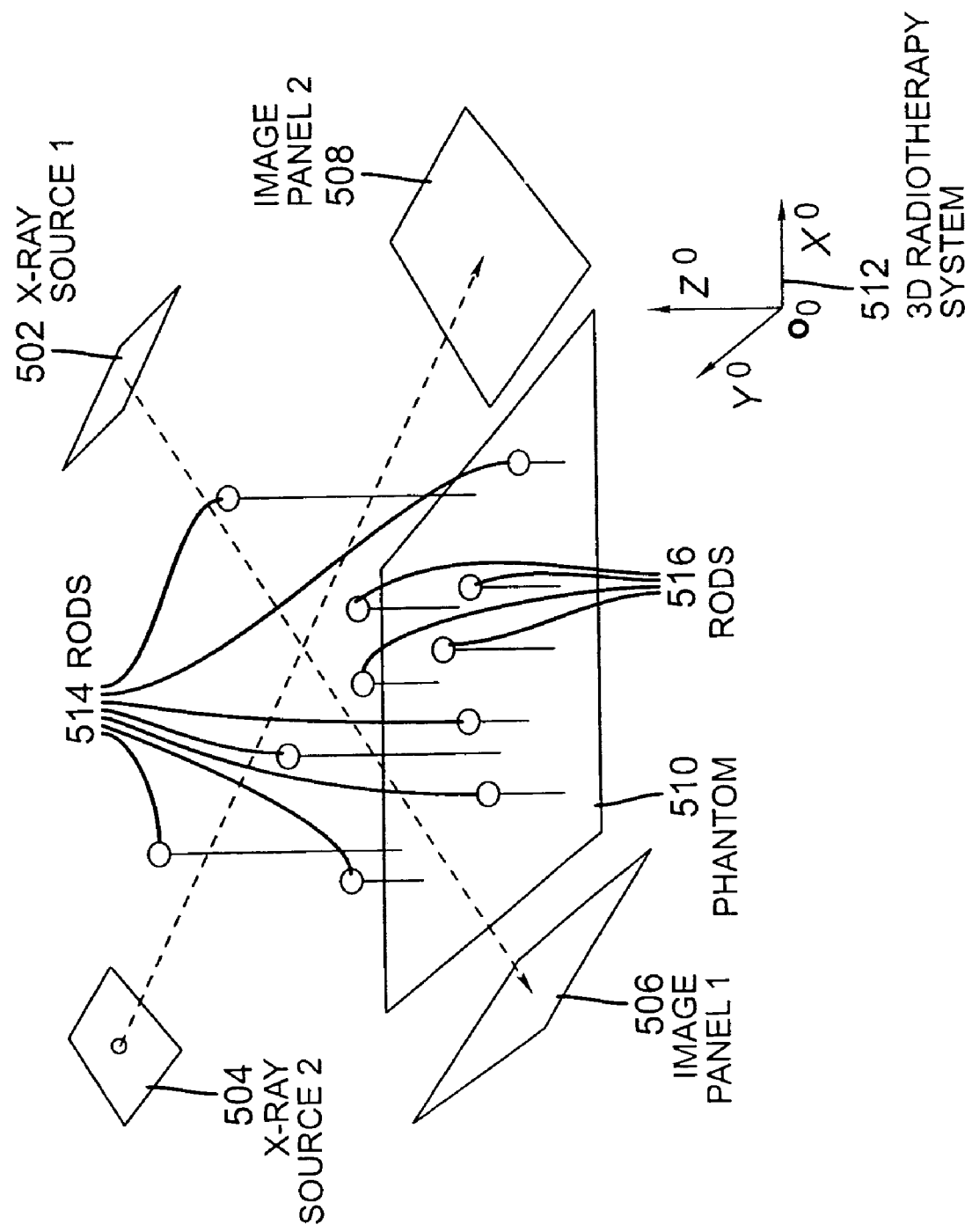
FIG. 5 is an illustration of an adjustable phantom for computing computational models of projective imaging devices of the second target identification system according to an exemplary embodiment of the current invention.

To obtain N, (N≧6), known non-coplanar 3D points, an adjustable phantom is developed (step 602). An illustrative phantom 510 is depicted in FIG. 5. The phantom 510 has a non-metallic base with threaded holes made on its surface. There are threaded non-metallic rods in the holes and metallic ball bearings of different diameters at the tips of the rods. The rods are of different heights. For different applications, for example, different sizes of X-ray detectors, additional rods can be added or inserted rods can be removed. The positions of the rods with respect to some reference points (e.g. corners of the base or some visible markers on the base (not shown)) and the heights of the rods are precisely measured using a high precision XYZ table, or laser measurement instrument. Some of the rods 514 are randomly selected as the known non-coplanar 3D points used for estimating the computational models $A_m$. Some other rods 516 are used as ground truth to test the precision of the models.

Before the radiotherapy treatment phase, the phantom is placed on the couch 111 and the position and orientation of the phantom 510 with respect to 3D radiotherapy system 512 (or 114, 212) are measured (step 604). With the projective imaging devices (X-ray imager pairs (502-506 and 504-508)), two radiographs of the phantom are captured (step 606). The 2D coordinates of the metallic ball bearings measured in the radiographs and the known 3D positions of the metallic ball bearings are used in Equation (7) (step 608) to compute 3D to 2D computational models $A_m$ with respect to the 3D radiotherapy system $(X^0, Y^0, Z^0)$ (512, 114, 212).

Figure 7:
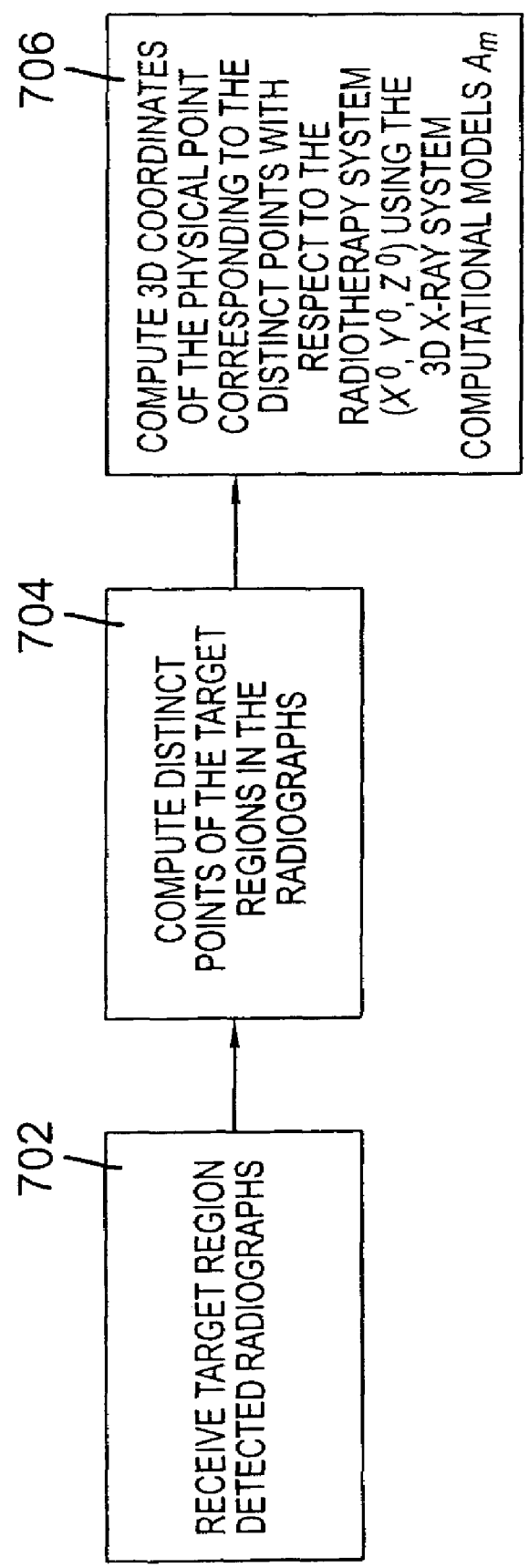
FIG. 7 is a flowchart illustrating the method of computing three-dimensional coordinates of a target according to an exemplary embodiment of the current invention.

FIG. 7 summarizes the workflow of estimating the 3D position of a target using 2D projections of its distinct points. In step 702 two radiographs with detected target regions are received. Distinct points (e.g. corners, centroids) of the target regions in the two radiographs are then computed in step 704. These distinct points are used in step 706 to calculate 3D coordinates of the corresponding physical points in the 3D coordinate system with the computational models estimated in step 608. Exemplary distinct points are $C^1$.position and $C^2$.position which are described previously.

Now turning back to FIG. 3A, the remaining steps of the method for target recognition are discussed. Step 316 receives the 3D position information of the target region from step 314 and morphological information, $C^1$.descriptor and $C^2$.descriptor, from step 310. Step 316 compares the received information with a treatment plan that is designed based on the identified target characteristics in the first target identification system. It then performs radiotherapy mode adaptation in response to the results of the comparison. The radiotherapy mode adaptation may include, but are not limited to, administering the dose, refraining from administering the dose, repositioning the patient, and redefining the therapeutic radiation beam shape. Concurrently, the 3D position information of the target region from step 314 and morphological information, $C^1$.descriptor and $C^2$.descriptor from step 310 are fed into step 318 where display devices are used to provide the patient and the oncologist with visual feedback of position and shape changes.

Recall that the control center 120 may include electronic and mechanical units used for controlling couch position, gantry rotation, X-ray imaging device position and orientation, and other devices such as in vitro respiration monitoring unit (not shown). It may also include signal and image processing, graphic user interface and input/output devices that are used to display information gathered in step 318 for oncologists.

Figure 9:
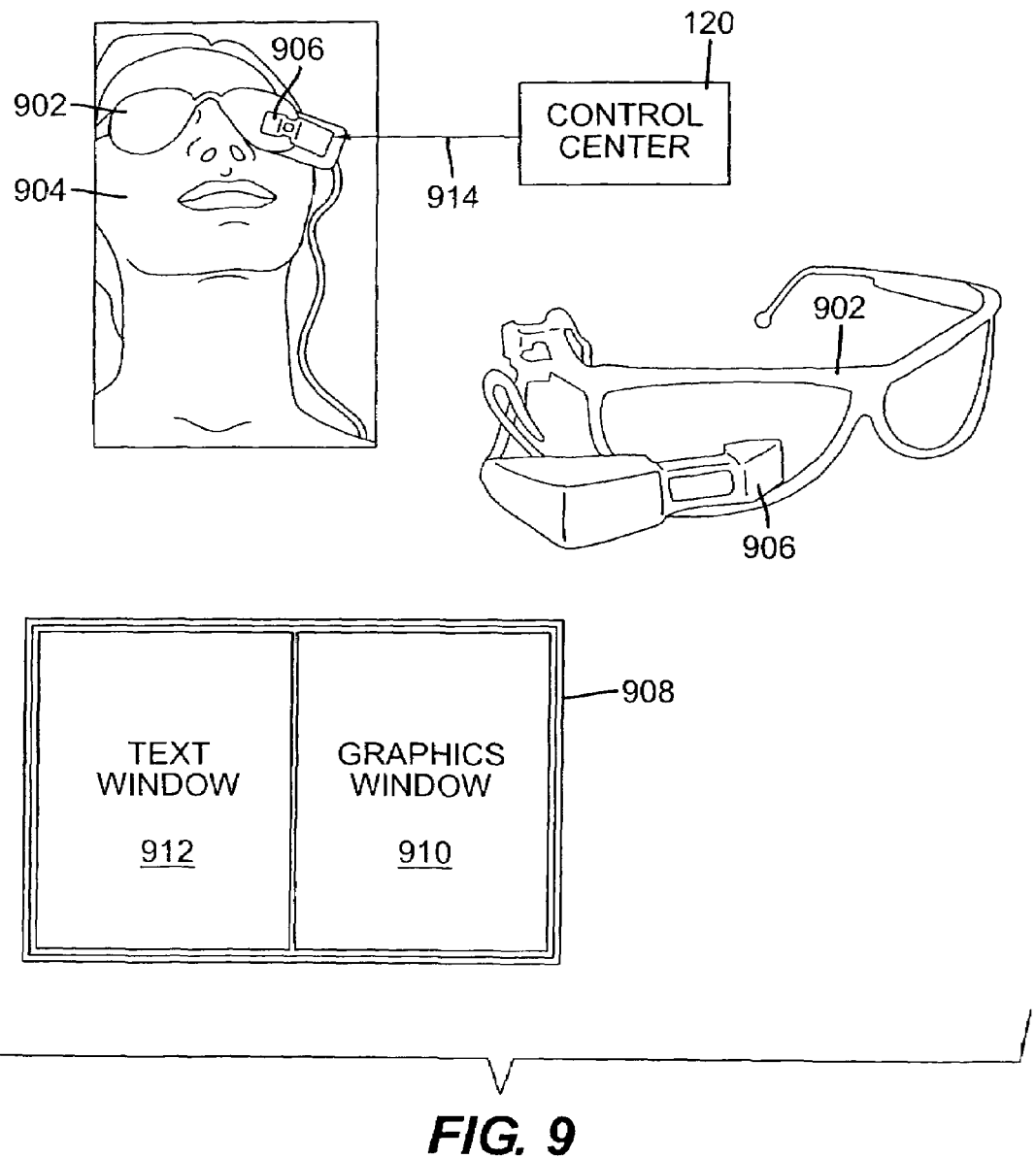
FIG. 9 is an illustration of visual feedback method according to an exemplary embodiment of the current invention.

As shown in FIG. 9, an exemplary device used in feedback visualization for the patient 904 is a head-up display 902 such as MicroOptical's SV-6 PC Viewer (see http://www.microopticalcorp.com/Products/HomePage.html). The head-up display 902 is worn by the patient 904. The patient receives information visually from a screen 906. Screen window 908 depicts an exemplary layout of the screen that has a graphics window 910 and a text window 912. Visible content shown in the graphics window 910 could be the shape and position of the target. Visible content shown in the text window could be instructions from the oncologist, status of the radiation process, time duration, and other medical related information. Visible content shown in the graphics window 910 could also be medical assistive (e.g. mind-soothing) information. Visible content shown in the text window could also be medical assistive information.

Graphics window 910 content display is manipulated by the oncologist through link 914 from the control center 120. Link 914 could be a physical cable connection or a wireless connection.

The method of target recognition essentially focus on reducing setup errors for radiotherapy by repositioning the body or modifying treatment plan with the identified target characteristics in the second target identification system. The problem of mitigating bodily process (e.g. respiration) caused irradiation uncertainty in real-time after initial setup remains to be addressed.

FIG. 3B is a flowchart illustrating one embodiment of the method of treatment target tracking for bodily process compensation of the present invention. Steps such as volumetric image acquisition, projective imaging device setup, producing projective radiographs etc. (301, 302, 303, 304, 305, 306, 308, 310, 312, 314) used in the method of target tracking were already detailed in previous discussions. Steps that are unique to the method of target tracking are explained next starting with the issue of real-time data collection.

The data collection of real-time projective radiographs using X-ray imager pairs 102-106 and 104-108 is regulated in steps 313 and 315. For a respiration cycle, data collection can be initiated when beginning to inhale and terminated at the end of exhale phase, or vise versa. The data collection process can continue for several cycles. The respiration cycle can be monitored by a breathing device such as an infrared sensing system with infrared markers placed on the body, or by a real-time respiration gating device (RPM) made by Varian. Data collection interval is determined in step 315 where irregular sampling pattern (different sampling rate) adopted to accommodate the nonlinear property of respiratory motion revealed in "Novel Prospective Respiratory Motion Correction Approach for Free-Breathing Coronary MR Angiography Using a Patient-Adapted Affine Motion Model" by D. Manke et al., Magnetic Resonance in Medicine, 2003; 50: 122-131.

Recall that in step 310, for patient setup error correction before radiation in the second system, the target characteristics identification is aided by the identified characteristics from the first system. While subsequent identification of target characteristics during the treatment can be aided by the previously identified target characteristics in the second system. Therefore there is a step 309 that performs an aid selection. If it is the initial data collection (for patient setup error correction), step 310 is executed where the target characteristics from the first system obtained in step 312 serves as the aid of identifying real-time target characteristics of the target in the second system. Otherwise, the process branches to step 311 where the target real-time target characteristics obtained in a previous data collection instance in step 311 serves as the aid (indicated by arrow 320) for identifying target characteristics of the target region in step 311 after acquiring a new set of real-time projective radiographs with X-ray imager pairs 102-106 and 104-108.

Denote data C obtained in the first system by $C_p^m$ and that in the second system by $C_t^m$. The real-time target tracking aid selection can be expressed as $$C_t^m(n) \leftarrow C_p^m; n=0$$

$$C_t^m(n+1) \leftarrow C_t^m(n); n>0$$

where $\leftarrow$ is a symbol signifying the operation of aiding the detection of target region, n=0 indicating the initial data collection, m=1,2 for two projective imaging devices.

The relevant members of the target characteristics data array are used in step 316 for radiotherapy mode adaptation that was detailed in the previous discussions.

The 3D position information of the target region from step 314 and morphological information, $C^1$.descriptor and $C^2$.descriptor from steps 310 and 311 are fed into step 318 where display devices are used to provide the patient and the oncologist with visual feedback of position and shape changes and other information.

The relevant members of the target characteristics data array are used in step 316 for radiotherapy mode adaptation that was detailed in the previous discussions.

The subject matter of the present invention relates to digital image processing and computer vision technologies, which is understood to mean technologies that digitally process a digital image to recognize and thereby assign useful meaning to human understandable objects, attributes or conditions, and then to utilize the results obtained in the further processing of the digital image.

The invention has been described in detail with particular reference to presently preferred embodiments, but it will be understood that variations and modifications can be effected within the scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

PARTS LIST

102 X-ray source 1
104 X-ray source 2
106 image panel 1
108 image panel 2
110 body
111 couch
112 gantry
114 3D radiotherapy system
120 control center
202 X-ray ($s_1$)
204 X-ray ($s_2$)
206 physical point ($p^k$)
208 line ($Z^1$)
210 line ($Z^2$)
212 3D world (radiotherapy) system ($X^0Y^0Z^0$)
214 3D local coordinate system ($X^2Y^2Z^2$)

216 3D local coordinate system ($X^1Y^1Z^1$)
218 center of image plane ($I_2$)
220 center of image plane ($I_1$)
222 projection ($q^1$)
224 projection ($q^2$)
301 capture volumetric image of body
302 exemplary setup
303 arrow
304 obtain information of virtual X-ray imager
305 arrow
306 produce projective radiographs
308 compute optional projective radiographs
310 identify target characteristics
312 identify target characteristics
314 calculate-target coordinates
316 perform radiotherapy mode adaptation
318 visual feedback
320 arrow
401 volumetric image
402 virtual x-ray source 1
404 virtual x-ray source 2
406 virtual image panel 1
408 virtual image panel 2
412 3D radiotherapy system
502 x-ray source 1
504 x-ray source 2
506 image panel 1
508 image panel 2
510 phantom
512 3D radiotherapy system
514 rods
516 rods
602 develop adjustable phantom
604 measure 3D radiotherapy device
606 take radiographs of phantom
608 compute 3D to 2D computational models
702 receive target region detected radiographs
704 compute distinct points of target regions in radiographs
706 compute 3D coordinates of physical point
800 target volume
802 projection
804 grid
806 start point
808 centroid
810 chaincode
820 coordinate system
822 coordinate system
824 horizontal scan line
826 vertical scan line
828 curve
830 curve
832 curve
838 curve
840 curve
842 curve
844 intersection point
846 intersection point
848 intersection point
850 intersection point
902 head-up display
904 patient
906 screen
908 screen window
910 graphics window
912 text window
914 link

The invention claimed is:

1. A system for radiation therapy with target recognition comprising:
a first three-dimensional (3D) image target identification system for obtaining first target characteristics that contains morphological and spatial information, texture and intensity features of the target within a patient body;
a second real-time 3D image target identification system for obtaining second target characteristics that contains morphological and spatial information, texture and intensity features of the target within the body aided by said first 3D image target characteristics;
computation means for calculation of three-dimensional coordinates of a target region with respect to a three-dimensional radiotherapy system using said second target characteristics;
irradiation means for radiotherapy mode adaptation in response to said second target characteristics and said calculation of three-dimensional coordinates of said target region; and
a human-machine interface, independent of patient body position, providing visual feedback of target 3D position and share in real time to the patient responsive to the radiation therapy.

2. A system for radiation therapy with target recognition comprising:
a first three-dimensional (3D) image target identification system for obtaining first target characteristics within a patient body;
a second real-time 3D image target identification system for obtaining second target characteristics within the body aided by said first 3D image target characteristics;
computation means for calculation of three-dimensional coordinates of a target region with respect to a three-dimensional radiotherapy system using said second target characteristics;
irradiation means for radiotherapy mode adaptation in response to said second target characteristics and said calculation of three-dimensional coordinates of said target region; and
a human-machine interface, independent of patient body position, providing visual feedback of target 3D position and shape in real time to the patient responsive to the radiation therapy,
wherein said first target identification system comprises:
a volumetric imaging device acquiring volumetric data of the body that contains the target;
two or more adjustable projective imaging devices of the first system; and
means of identifying target characteristics in a projective space of the first system.

3. A system for radiation therapy with target recognition comprising:
a first three-dimensional (3D) image target identification system for obtaining first target characteristics within a patient body;
a second real-time 3D image target identification system for obtaining second target characteristics within the body aided by said first 3D image target characteristics;
computation means for calculation of three-dimensional coordinates of a target region with respect to a three-dimensional radiotherapy system using said second target characteristics;
irradiation means for radiotherapy mode adaptation in response to said second target characteristics and said calculation of three-dimensional coordinates of said target region; and a human-machine interface providing visual feedback to the patient responsive to the radiation therapy,
wherein said first target identification system comprises;
   a volumetric imaging device acquiring volumetric data of the body that contains the target;
   two or more adjustable projective imaging devices of the first system; and
   means of identifying target characteristics in a projective space of the first system, and
wherein said second target identification system comprising:
   two or more adjustable projective imaging devices of the second system; and
   means of identifying target characteristics in projective radiographs of the second system aided by the identified target characteristics of the first system.

4. The system for radiation therapy with target recognition according to claim 3 further comprising calibration means for said first and second target identification systems that sets up the projective imaging devices of the first system and the projective imaging devices of the second system in a same projective manner in terms of projective geometry.

5. The system for radiation therapy with target recognition according to claim 4 wherein said computation means for calculation of three-dimensional coordinates of said target region comprises:
   an adjustable phantom that has a plurality of physical markers whose three-dimensional coordinates with respect to said three-dimensional radiotherapy system are precisely known and whose images can be acquired by said two or more projective imaging devices of the second system;
   means of determining computational models of said two or more projective imaging devices of the second system aided by placing said adjustable phantom in the projective path of said two or more projective imaging devices of the second system;
   means of optimally calculating three-dimensional coordinates of said target region by using the determined computational models of said two or more projective imaging devices of the second system and members of the said second target characteristics; and
   computational models to find a relationship between the three-dimensional space to two-projectional space, and using non-coplanar markers.

6. The system for radiation therapy with target recognition according to claim 1 wherein irradiation means for radiotherapy mode adaptation in response to said target characteristics obtained by the second system and said calculation of three-dimensional coordinates of said target region comprising:
   means of comparing said second target characteristics with said first target characteristics; and
   means of determining irradiation operation based on the result of the comparison.

7. The system of claim 1 wherein said first and second target characteristics comprise:
   members selected from a group consisting of: size of area, gradients, texture, surface and statistics, spatial and morphological parameters in 2D coordinates;
   functions that operate on members of target characteristics including image and computer vision operations select from a group consisting of: classification, segmentation, registration, detection, and parameters associated with these operations; and
   metadata that records time stamps and device specifications.

8. The system of claim 5 wherein said computation means for calculation of three-dimensional coordinates of said target region implicitly utilizes extrinsic and intrinsic parameters of the projective imaging means of the second system.

9. The system of claim 5 wherein said adjustable phantom further comprises:
   detachable markers of different height; and
   reconfigurable marker distribution patterns.

10. The system of claim 5 wherein said means of determining computational models of said two or more projective imaging devices of the second system comprises:
   means for acquiring two or more radiographs of the phantom with said two or more projective imaging devices of the second system;
   means for identifying a plurality of projections of the markers of the phantom in said acquired radiographs;
   means for finding a plurality of corresponding projections of the markers in the radiographs; and
   means for computing computational models of said two or more projective imaging devices with the corresponding projections of the markers and the known 3D locations of the markers.

11. The system of claim 5 wherein means of calculation of three-dimensional coordinates of said target region comprises:
   means for acquiring two or more real-time radiographs of the patient body with said two or more projective imaging devices of the second system;
   means for identifying target regions within said acquired radiographs;
   means for finding one or more pairs of corresponding points in the identified target regions; and
   means for computing three-dimensional coordinates of one or more corresponding physical points of the patient body with said one or more pairs of corresponding points in the identified target regions using the computed computational models of said two or more projective imaging devices of the second system.

12. The system of claim 5 wherein said means of calculation of three-dimensional coordinates of said target region comprises means for comparing the calculated three-dimensional coordinates of said target region with an isocenter above the treatment couch in the three-dimensional radiotherapy system.

13. The system of claim 6 wherein said irradiation means for radiotherapy mode adaptation comprises:
   means for acquiring a volumetric image of the patient body;
   means for delineating the target volume;
   means for computing target contour curves in a two-dimensional plane in the first system; and
   means for calculating a descriptor for said target contour in the first system.

14. The system of claim 6 wherein means of comparing said target characteristics comprises:
   means for acquiring one or more radiographs of the patient body with one or more projective imaging devices of the second system;
   means for identifying target regions in said one or more radiographs;
   means for finding contour descriptors for said target regions; and
   means for comparing said contour descriptors with a target reference contour descriptor.

15. The system of claim 14 wherein said target reference contour descriptor is said calculated target contour descriptor with the volumetric patient body image in the first system.

16. The system of claim 6 wherein means of determining irradiation operation comprises means for administering a dose, means for refraining from administering a dose, means for repositioning the patient, and means for redefining the therapeutic radiation beam shape based on the result of the comparison.

17. The system of claim 13 wherein said computing target contour curves in said two-dimensional plane in the first system comprises:
- means for defining a local target 3D coordinate system whose axes are parallel to that of a projective imaging device of the first system;
- means for finding surface curves of the delineated target volume surface in the planes that are parallel to a projection plane of the projective imaging device of the first system;
- means for collapsing all the found surface curves to a common two-dimensional plane that is parallel to the projection plane of the projective imaging device of the first system along a direction perpendicular to said plane;
- means for scanning the common plane horizontally and vertically along horizontal and vertical scan lines respectively; and
- means for collecting outmost intersecting points of said collapsed curves and said scan lines, and save the collected points to a contour points list.

18. The system of claim 1 wherein the human-machine interface comprises:
- a control center; and
- a visual feedback mechanism.

19. The system of claim 18 wherein said control center comprises:
- means for controlling position, orientation and operations for devices;
- means for signal and image processing; and
- graphic user interface and input/output devices for users.

20. The system of claim 2 wherein the human-machine interface comprises a control center, and a visual feedback mechanism, and
- wherein said visual feedback mechanism comprises:
  - a wearable monitoring device worn by the patient,
  - a communication link between the wearable monitoring device and the control center;
  - a screen for displaying visual information to the patient; and
  - said visual information is related to radiation therapy process.

21. The system of claim 20 wherein said screen displaying visual information to the patient comprises:
- means for displaying said identified target characteristics of the second system; and
- means for displaying other information than said identified target characteristics of the second system.

22. A system for radiation therapy with target tracking comprising:
- a first three-dimensional (3D) image target identification system for obtaining target characteristics within a patient body;
- a second 3D image real-time target identification system for obtaining target characteristics within the body in response to said first 3D image target characteristics;
- computation means for calculation of three-dimensional coordinates of said target region with respect to a three-dimensional radiotherapy system using said target characteristics obtained by the second target identification system;
- data collection means for obtaining an array of target characteristics during a bodily process;
- radiotherapy mode adaptation means in response to said array of target characteristics; and
- a human-machine interface, independent of patient body position, providing visual feedback of changes of target 3D position and shape in real-time to the patient responsive to the radiation therapy.

23. A system for radiation therapy with target tracking comprising:
- a first three-dimensional (3D) image target identification system for obtaining target characteristics within a patient body;
- a second 3D image real-time target identification system for obtaining target characteristics within the body;
- computation means for calculation of three-dimensional coordinates of said target region with respect to a three-dimensional radiotherapy system using said target characteristics obtained by the second target identification system;
- data collection means for obtaining an array of target characteristics during a bodily process;
- radiotherapy mode adaptation means in response to said array of target characteristics; and
- a human-machine interface, independent of patient body position, providing visual feedback of changes of target 3D position and shape in real-time to the patient responsive to the radiation therapy,
- wherein said first target identification system comprises:
  - a volumetric imaging device acquiring volumetric data of the body that contains the target;
  - two or more adjustable projective imaging devices of the first system; and
  - means of identifying target characteristics in the projective space of the first system.

24. A system for radiation therapy with target tracking comprising:
- a first three-dimensional (3D) image target identification system for obtaining target characteristics within a patient body;
- a second 3D image real-time target identification system for obtaining target characteristics within the body in response to said first 3D image target characteristics;
- computation means for calculation of three-dimensional coordinates of said target region with respect to a three-dimensional radiotherapy system using said target characteristics obtained by the second target identification system;
- data collection means for obtaining an array of target characteristics during a bodily process;
- radiotherapy mode adaptation means in response to said array of target characteristics; and
- a human-machine interface providing visual feedback to the patient responsive to the radiation therapy, and
- wherein said second target identification system comprises:
  - two or more adjustable projective imaging devices of the second system;
  - means of identifying target characteristics in the projective radiographs of the second system aided by the identified target characteristics of the first system; and
  - means of identifying target characteristics in projective radiographs of the second system aided by the previously identified target characteristics of the second system.

* * * * *